(12) United States Patent
Papini et al.

(10) Patent No.: US 7,037,893 B2
(45) Date of Patent: May 2, 2006

(54) GLYCOPEPTIDES, THEIR PREPARATION AND USE IN THE DIAGNOSIS OR THERAPEUTIC TREATMENT OF MULTIPLE SCLEROSIS

(75) Inventors: Anna Maria Papini, Florence (IT); Mario Chelli, Incisa Val d'Arno (IT); Paolo Rovero, Florence (IT); Francesco Lolli, Florence (IT)

(73) Assignee: Universita' Degli Studi Di Firenze, Florence (IT)

( * ) Notice: Subject to any disclaimer, the term of this patent is extended or adjusted under 35 U.S.C. 154(b) by 0 days.

(21) Appl. No.: 10/482,044

(22) PCT Filed: Jun. 19, 2002

(86) PCT No.: PCT/EP02/06767

§ 371 (c)(1),
(2), (4) Date: Dec. 22, 2003

(87) PCT Pub. No.: WO03/000733

PCT Pub. Date: Jan. 3, 2003

(65) Prior Publication Data

US 2004/0235713 A1   Nov. 25, 2004

(30) Foreign Application Priority Data

Jun. 22, 2001   (IT) ............................ FI2001A0114

(51) Int. Cl.
*A61K 38/16* (2006.01)
*A61K 38/00* (2006.01)
*A61K 31/14* (2006.01)
*A01N 37/18* (2006.01)
*A01N 33/12* (2006.01)

(52) U.S. Cl. .............................. 514/8; 514/2; 514/643; 424/279.1

(58) Field of Classification Search ................... 514/8; 424/279.1

See application file for complete search history.

(56) References Cited

FOREIGN PATENT DOCUMENTS

| WO | WO9735879 | 10/1997 |
|---|---|---|
| WO | WO9957241 | 11/1999 |
| WO | WO0012126 | 3/2000 |
| WO | WO03000733 | 1/2003 |

OTHER PUBLICATIONS

Web site info: www.mimotopes.com/peptides/mods.html (see attached).*
U.S. Appl. No. 10/483,803, filed Jan. 2004, D'alessio et al.*
Mazzucco et al., "A Synthetic Glycopeptide of Human Myelin Oligodendrocyte Glycoprotein to Detect Antibody Responses in Multiple Sclerosis and Other Neurological Diseases", Bioorganic & Medicinal Chemistry Letters, 9, pp. 167-172, (1999).

* cited by examiner

*Primary Examiner*—Christopher R Tate
*Assistant Examiner*—Marcela M Cordero Garcia
(74) *Attorney, Agent, or Firm*—Abelman, Frayne & Schwab

(57) ABSTRACT

Glycopeptides capable of identifying multiple sclerosis antibodies, and therefore useful as diagnostic tools or for the treatment of said pathology are described.

18 Claims, No Drawings

SEQUENCE LISTING

<160> NUMBER OF SEQ ID NOS: 8

<210> SEQ ID NO 1
<211> LENGTH: 21
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
<222> LOCATION: (7)..(7)
<223> OTHER INFORMATION: the carbohydrate is beta-D-glucopyranosyl

<400> SEQUENCE: 1

Thr Pro Arg Val Glu Arg Asn Gly His Ser Val Phe Leu Ala Pro Tyr
1               5                   10                  15

Gly Trp Met Val Lys
            20

<210> SEQ ID NO 2
<211> LENGTH: 21
<212> TYPE: PRT
<213> ORGANISM: Artificial Sequence
<220> FEATURE:
<223> OTHER INFORMATION: GLYCOPEPTIDE
<220> FEATURE:
<221> NAME/KEY: CARBOHYD
<222> LOCATION: (7)..(7)
<223> OTHER INFORMATION: the carbohydrate is beta-D-glucopyranosyl
<220> FEATURE:
<221> NAME/KEY: MISC_FEATURE
<222> LOCATION: (5)..(5)
<223> OTHER INFORMATION: Xaa is diamino propanoic acid

<400> SEQUENCE: 2

Thr Pro Arg Val Xaa Arg Asn Gly His Asp Val Phe Leu Ala Pro Tyr
1               5                   10                  15

Gly Trp Met Val Lys
            20

<210> SEQ ID NO 3
<211> LENGTH: 21
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
<222> LOCATION: (7)..(7)
<223> OTHER INFORMATION: the carbohydrate is beta-D-glucopyranosyl
<220> FEATURE:
<221> NAME/KEY: MISC_FEATURE
<222> LOCATION: (10)..(10)
<223> OTHER INFORMATION: Xaa is Orn

<400> SEQUENCE: 3

Thr Pro Arg Val Asp Arg Asn Gly His Xaa Val Phe Leu Ala Pro Tyr
1               5                   10                  15

Gly Trp Met Val Lys
            20

<210> SEQ ID NO 4
<211> LENGTH: 13
<212> TYPE: PRT
<213> ORGANISM: Artificial Sequence
<220> FEATURE:
<223> OTHER INFORMATION: glycopeptide

```
<220> FEATURE:
<221> NAME/KEY: CARBOHYD
<222> LOCATION: (6)..(6)
<223> OTHER INFORMATION: the carbohydrate is beta-D-glucopyranosyl

<400> SEQUENCE: 4

Ala Lys Thr Ala Lys Asn Gly His Val Glu Ala Ser Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
<222> LOCATION: (2)..(2)
<223> OTHER INFORMATION: the carbohydrate is beta-D-glucopyranosyl

<400> SEQUENCE: 5

Glu Asn Pro Val Val His Phe Phe Lys Asn Ile Val Thr Pro Arg Thr
1               5                   10                  15

Pro

<210> SEQ ID NO 6
<211> LENGTH: 11
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
<222> LOCATION: (2)..(2)
<223> OTHER INFORMATION: the carbohydrate is beta-D-glucopyranosyl

<400> SEQUENCE: 6

Asp Asn Pro Val Glu Ala Phe Lys Gly Ile Ser
1               5                   10

<210> SEQ ID NO 7
<211> LENGTH: 22
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
<222> LOCATION: (7)..(7)
<223> OTHER INFORMATION: the carbohydrate is beta-D-glucopyranosyl
<220> FEATURE:
<221> NAME/KEY: MISC_FEATURE
<222> LOCATION: (11)..(11)
<223> OTHER INFORMATION: Xaa is 7-aminoheptanoic acid

<400> SEQUENCE: 7

Thr Pro Arg Val Glu Arg Asn Gly His Ser Xaa Val Phe Leu Ala Pro
1               5                   10                  15

Tyr Gly Trp Met Val Lys
            20

<210> SEQ ID NO 8
<211> LENGTH: 15
<212> TYPE: PRT
<213> ORGANISM: Artificial Sequence
<220> FEATURE:
<223> OTHER INFORMATION: glycopeptide
<220> FEATURE:
<221> NAME/KEY: CARBOHYD
```

-continued

```
<222> LOCATION: (2)..(2)
<223> OTHER INFORMATION: the carbohydrate is beta-D-glucopyranosyl
<220> FEATURE:
<221> NAME/KEY: MISC_FEATURE
<222> LOCATION: (13)..(15)
<223> OTHER INFORMATION: Xaa is beta-Ala

<400> SEQUENCE: 8

Asp Asn Pro Val Val His Phe Phe Lys Asn Ile Val Xaa Xaa Xaa
1               5                   10                  15
```

GLYCOPEPTIDES, THEIR PREPARATION AND USE IN THE DIAGNOSIS OR THERAPEUTIC TREATMENT OF MULTIPLE SCLEROSIS

FIELD OF INVENTION

The present invention refers to glycopeptides formed of 11–24 aminoacids capable of identifying multiple sclerosis antibodies and therefore useful as diagnostic tools or for the treatment of said pathology.

STATE OF THE ART

Multiple sclerosis (MS) is an inflammatory demyelinating disease of the central nervous system highly invalidating and therefore of high social impact. It causes the degradation of the central nervous system white matter (myelin) bringing about serious damage in the transmission of nerve signals.

The etiopathogenesis of the disease has not yet been clearly defined, but it is hypothesised that an autoimmune process directed against the principal myelin proteins is an important pathogenic mechanism of the disease. The myelin damage is most probably due to the synergic action of the T cell response and the antibody response against myelin proteins and glycoproteins. In particular the autoantibodies can play a key role in the activation of macrophages, in demyelinization, and in the blocking of nervous conduction.

In a previous study [A. M. Papini et al., Proceedings of the 10$^{th}$ International Congress of Immunology, Monduzzi Editore, International Proceeding Division Bologna, Italy (1998), pp. 1239–1244] the possibility of identifying MS specific antibodies through a glycosylated peptide constituted of a sequence of 21 aminoacids of the myelin oligodendrocytic glycoprotein (MOG) (from positions 30 to 50), and indicated by the formula Asn$^{31}$(Glc)hMOG(30–50) has been demonstrated.

The interest in developing new glycosylated peptides capable of carrying out the function of identifying said antibodies with greater efficiency and therefore useful both for the diagnosis and for the treatment of multiple sclerosis is evident.

SUMMARY OF THE INVENTION

The present invention refers to glycopeptides of 11–24 aminoacids containing a tetrapeptide of formula (I):

X-Asn(G)-Y-Z      (I)

in which:
X=aminoacid carrying an amino or carboxylic group on the side chain;
Y=Pro, Gly;
G is a sugar
Z=Ala, Val, Ile, His

DETAILED DESCRIPTION OF THE INVENTION

It has now been surprisingly found, and is a subject of the present invention, that short glycopeptides, constituted of 11–24 aminoacids, containing the above-defined tetrapeptide play a very efficient role in the recognition of the antibodies typical of MS and are therefore useful in its diagnosis or its therapeutic treatment.

According to the present invention, glycopeptides of formula (II) are preferred:

A-B-X-Asn(G)-Y-Z-C-D      (II)

in which:
Y and G are as defined above;
A=2–5 aminoacids or absent
B and C=trifunctional aminoacids forming a lactam bridge between each other by means of the respective side chains, or absent;
D=5–15 aminoacids;
X=Glu, Asp, Lys, Arg, Orn, Dap;
Z=Ala, Val, Ile, His.

For trifunctional aminoacids forming a lactam bridge between each other as defined above, is meant, for example, the pair Dap-Asp or Asp-Dap, Dab-Glu or Glu-Dab, Orn-Asp or Asp-Orn, and the pair formed by other aminoacids, for example non-natural aminoacids, having analogous characteristics.

For sugar is preferably meant: mono and disaccharides of type Glc, GlcNAc, β-D-Glcp-(1→4)-D-Glc (cellobiose), etc.

For aminoacids, when not otherwise defined, is meant natural or non-natural aminoacids.

Obviously residues A, if present, and D may contain an appropriate alkyl spacer to lengthen the chain, where for alkyl spacer, in the sense used herein, is meant ω-aminoacids with linear alkyl chains ($H_2N$—$(CH_2)_n$—$CO_2H$ where n is 2–6.

The presence of the formula (I) tetrapeptide as defined above, can induce a folding in the peptide conformation that can, for this reason, assume a "hook like" form (when the tetrapeptide is present in the terminal portion of the peptide) or "a hairpin like" form (when the tetrapeptide is present in the central portion of the peptide). These conformations allow an optimal binding of the patients' autoantibodies; this fact is essential for the unexpected properties of the peptides according to the invention.

Particularly preferred, according to the invention are the peptides represented by the following sequences:

H-Thr-Pro-Arg-Val-Glu-Arg-Asn(Glc)-Gly-His-Ser-Val-Phe-Leu-Ala-Pro-Tyr-Gly-Trp-Met-Val-Lys-OH (SEQ ID NO: 1)

H-Thr-Pro-Arg-Val-cyclic[Dap-Arg-Asn(Glc)-Gly-His-Asp]-Val-Phe-Leu-Ala-Pro-Tyr-Gly-Trp-Met-Val-Lys-OH (SEQ ID NO: 2)

H-Thr-Pro-Arg-Val-cyclic[Asp-Arg-Asn(Glc)-Gly-His-Orn]-Val-Phe-Leu-Ala-Pro-Tyr-Gly-Trp-Met-Val-Lys-OH (SEQ ID NO: 3)

H-Ala-Lys-Thr-Ala-Lys-Asn(Glc)-Gly-His-Val-Glu-Ala-Ser-Gly-OH (SEQ ID NO: 4)

H-Glu-Asn(Glc)-Pro-Val-Val-His-Phe-Phe-Lys-Asn-Ile-Val-Thr-Pro-Arg-Thr-Pro-OH (SEQ ID NO: 5)

H-Asp-Asn(Glc)-Pro-Val-Glu-Ala-Phe-Lys-Gly-Ile-Ser-OH (SEQ ID NO: 6)

H-Thr-Pro-Arg-Val-Glu-Arg-Asn(Glc)-Gly-His-Ser-HN-$(CH_2)_6$-CO-Val-Phe-Leu-Ala-Pro-Tyr-Gly-Trp-Met-Val-Lys-OH (SEQ ID NO: 7)

H-Asp-Asn(Glc)-Pro-Val-Val-His-Phe-Phe-Lys-Asn-Ile-Val-(βAla)$_3$-OH (SEQ ID NO: 8)

The peptides as defined above can also contain an —HN—$(CH_2)_n$—$CO_2H$ group in the C-terminus (where n=2–6) so as to allow the attachment to a resin as requested for their practical use in diagnostics or in therapeutic treatments.

The peptides according to the invention can be prepared according to known methods for solid or liquid phase synthesis.

The solid phase method is particularly useful, well known to experts in the field, the basis of which is that the C-terminal tesidue is covalently bound to an appropriate solid support, for example polystyrene (Wang's ® resin), polystyrene-polyoxyethylene (TentaGel® resin or PEG-PS) or polyethylene glycol and polyacrylaminde co-polymers (PEGA resin), and the successive aminoacids are added sequentially, through acylation of the amino group of the residue bound to the resin, for example through the symmetric anhydride of the following aminoacid, appropriately protected, where necessary, on the side chain. Upon completion of the synthesis the crude peptide is obtained by treating the resin with an appropriate acid, for example hydrofluoric acid or trifluoroacetic acid, and separated by precipitation in ethyl ether and successive lyophilisation. The peptide is finally purified using chromatographic techniques, such as for example preparative HPLC. It is also possible to maintain the synthetic peptide bound to the solid support (for example polystyrene-polyoxyethylene TentaGel® resin or PEG-PS), carrying out the selective deprotection of the side chains with an appropriate reagent.

Alternatively, still according to known techniques, the attachment of the peptide to the appropriate support is achieved so as to form the corresponding conjugates, useful in diagnostics or in therapy. The preferred supports for this purpose include resins, insoluble in water, and completely compatible with organic liquids, such as: silica gel, cellulose, polyacrylate, sepharose and analogues, as well as the same resins normally used by experts in the field for the preparation of synthetic peptides, as for example Wang's resin, polystyrene-polyoxyethylene (TentaGel® resin or PEG-PS) or polyethylene glycol and polyacrylamide copolymers (completely compatible with water) such as PEGA resin and more stable analogue resins such as POEPS (polyoxyethylene-polystyrene), POEPOP (polyoxyethylene-polyoxypropylene), as well as macroporous resins described for their interest for the solid phase glycosylation of peptides, such as SPOCC (PEG substituted with oxethane) [Rademann, J; Grøtli, M; Meldal, M; and Bock, K. J. Am. Chem. Soc. 1999, 121, 5459–5466] or derivatives thereof like EXPO$_{3000}$ (copolymer with tetrakis-[4-(3-methyl-oxethane-3-ylmethyl)-phenyl]-silane) [Tornøe, C. W.,; and Meldal M. In: Peptides 2000, J. Martinez and J. A. Fehrentz (Eds.) EDK, Paris, France 2001].

Examples disclosing the preparation of some peptides according to the invention, are provided in the following for illustrative, non limiting purposes of the invention.

EXAMPLE 1

Synthesis of a Linear Peptide

Preparation of H-Thr-Pro-Arg-Val-Glu-Arg-Asn(Glc)-Gly-His-Ser-Val-Phe-Leu-Ala-Pro-Tyr-Gly-Trp-Met-Val-Lys-OH (SEQ ID NO: 1)

The resin Fmoc-Lys(Boc)-NovaSyn (0.5 g, 0.11 mmol/g) was made to swell in DMF for 1 hour at room temperature and packed into the glass column (150×15 mm) of a continuous flow, semiautomated synthesiser. After deprotection of the amino group present on the resin with a solution of 20% piperidine in DMF, for the insertion of each aminoacid the column was loaded with a solution containing Fmoc-aminoacid (2.5 eq., 0.137 mmol) dissolved in DMF (1.3 ml), and as activating reagent HOBt (2.5 eq, 0.137 mmol), TBTU (2.5 eq, 0.137 mmol) and NMM (3.75 eq, 0.205 mmol).

The following aminoacids were used in order:
1) Fmoc-Val-OH
2) Fmoc-Met-OH
3) Fmoc-Trp(Boc)-OH
4) Fmoc-Gly-OH
5) Fmoc-Tyr(tBu)-OH
6) Fmoc-Pro-OH
7) Fmoc-Ala-OH.
8) Fmoc-Leu-OH
9) Fmoc-Phe-OH
10) Fmoc-Val-OH
11) Fmoc-Ser(tBu)-OH
12) Fmoc-His(Trt)-OH
13) Fmoc-Gly-OH
14) Fmoc-Asn(Glc)-OH (N$^\alpha$-Fmoc-N$^\gamma$-(2,3,4,6-tetra-O-acetyl-β-D-glucopyranosyl)-L-Asn-OPfp)
15) Fmoc-Arg(Pmc)-OH
16) Fmoc-Glu(OtBu)OH.
17) Fmoc-Val-OH
18) Fmoc-Arg(Pmc)-OH
19) Fmoc-Pro-OH.
20) Fmoc-Thr(tBu)-OH Upon completion of synthesis, the resin was deprotected with 20% piperidine in DMF, filtered, washed with DMF, DCM and ether, and finally dried under vacuum. The crude peptide was obtained by treatment of the resin with a mixture of TFA/phenol/anisole/ethanedithiol (94:2:2:2) (10 ml), maintained with agitation for 30 minutes at 0° C. and at room temperature for 1.5 hours. The resin was filtered and washed with TFA and the filtrate concentrated to half volume under vacuum. The peptide was precipitated by treatment with cold ether. The precipitate obtained was lyophilised recovering 112 mg of crude peptide.

Deacetylation was attained by adding dropwise, a solution of NaOMe 0.1 M in MeOH, to achieve a pH=12, to a solution of the peptide in anhydrous MeOH (15 ml) maintained with agitation in a nitrogen atmosphere. The NaOMe solution was prepared by adding metallic sodium (270 mg in ligroin (pet. ether), 117 mmol) to distilled MeOH (11 ml) in a nitrogen atmosphere. After 1 hour dry ice was added to the mixture until neutralised. The solution was concentrated giving the crude peptide, which was purified by semi-preparative HPLC (HPLC purity greater than 97%).

Characterisation: ESI-MS: found: [M+3H]3+m/z=869.9, [M+2H]2+m/z=1304.2; calculated: PM monoisotopic=2605.38.

The other linear peptides were prepared following the same method, but using the necessary aminoacids in the appropriate sequences.

EXAMPLE 2

Synthesis of a Cyclic Peptide

Preparation of H-Thr-Pro-Arg-Val-cyclic[Dap-Arg-Asn (Glc)-Gly-His-Asp]-Val-Phe-Leu-Ala-Pro-Tyr-Gly-Trp-Met-Val-Lys-OH (SEQ ID NO: 2)

TentaGel resin SPHB-Lys(Boc)-Fmoc (1.00 g, 0.22 mmol/g) was treated as described in example 1. For each coupling 4 eq of Fmoc-aminoacids (0.88 mmol) dissolved in DMF (1.3 ml) were used, and as activating reagents HOBt (4 eq, 0.88 mmol) and TBTU (4 eq, 0.88 mmol,) and NMM (6 eq, 1.68 mmol,) were used.

The following aminoacids were used in the following order:
1) Fmoc-Val-OH
2) Fmoc-Met-OH
3) Fmoc-Trp(Boc)-OH
4) Fmoc-Gly-OH
5) Fmoc-Tyr(tBu)-OH
6) Fmoc-Pro-OH
7) Fmoc-Ala-OH
8) Fmoc-Leu-OH
9) Fmoc-Phe-OH
10) Fmoc-Val-OH
11) Fmoc-Asp(OAll)-OH
12) Fmoc-His(Trt)-OH
13) Fmoc-Gly-OH
14) Fmoc-Asn(Glc)-OPfp
15) Fmoc-Arg(Pmc)-OH
16) Fmoc-Dap(Alloc)-OH
17) Fmoc-Val-OH
18) Fmoc-Arg(Pmc)-OH
19) Fmoc-Pro-OH
20) Fmoc-Thr(tBu)-OH Upon completion of synthesis, the allylic protective groups of the Dap and Asp side chains were selectively removed by treatment with a solution of Pd(PPh3)4 (3 eq) in 7.5 ml of CHCl3/AcOH/NMM 37:2:1 in Argon atmosphere. The reaction mixture was stirred using a mechanical arm for 3 hours at room temperature. The resin was then filtered and washed three times with a solution of 0.5% DIPEA in DMF, three times with a solution of 0.05% sodium diethyl carbamate in DMF, three times with DMF and three times with DCM.

For the subsequent cyclysation reaction, the resin was made to swell in a flask in DMF for 1 hour. NMM (4 eq.) was then added and after 10 minutes, PyBOP (4 eq.). The reaction mixture was agitated, using a mechanical arm, for three days at room temperature. The resin was filtered and washed several times with DMF, DCM and Et2O and finally dried under vacuum.

Afterwards, the resin was deprotected of Fmoc by 20% piperidine in DMF, followed by detachment of the peptide and its isolation exactly as described in example 1.

EXAMPLE 3

Synthesis of a Resin-Bound Peptide

Preparation of H-Thr-Pro-Arg-Val-Glu-Arg-Asn(Glc)-Gly-His-Ser-Val-Phe-Leu-Ala-Pro-Tyr-Gly-Trp-Met-Val-Lys-($\beta$Ala)$_3$-PEG-PS (SEQ ID NO: 4)

The base resin PEG-PS, in amino form (1 g, 0.09 eq) was made to swell in DMF s for 1 hour at room temperature and packed into the glass column (150×15 mm) of a continuous flow, semiautomatic synthesiser. For the coupling of the first aminoacid the column was loaded with a solution containing Fmoc-$\beta$Ala-OH (4 eq., 0.36 mmol) dissolved in DMF (1.5 ml), and as activating reagents HOBt (4 eq., 0.36 mmol), TBTU (4 eq., 0.36 mmol) and NMM (6 eq, 0.54 mmol). The reaction was carried out for 1 hour and later, after the appropriate washes, followed by the deprotection of the amino groups, by treatment with 20% piperidine in DMF. The coupling cycle for $\beta$Ala was repeated a further twice, and then continued in the same way for the coupling of a residue of Fmoc-Lys(Boc)-OH. Later, the construction of the entire peptide sequence was continued, exactly as indicated in example 1. Following the final treatment with piperidine, the resin-peptide was deprotected by treatment with a mixture of TFA/phenol/anisole/ethanedithiol (94:2:2:2) (10 ml), with agitation for 30 minutes at 0° C. and at room temperature for 1.5 hours, scrupulously washed and dried under reduced pressure.

EXAMPLE 4

Conjugation of a Peptide to Resin

A free peptide, linear or cyclic, prepared as described in examples 1 and 2, respectively, was conjugated to sepharose resin preactivated with CNBr, according to the usual reaction protocols advised by the manufacturers in order to obtain a resin-peptide conjugate. The product thus obtained is useful as for example for the preparation of plates for the diagnosis or treatment of patients affected by MS [see also the following].

The present invention refers also to a kit comprising the glycopeptides according to the invention and useful for diagnostic purposes.

According to a preferred embodiment of the invention a kit as above said comprises:
a microplate
a buffer solution for adhering the peptide to the plate;
a modified peptide according to the invention (lyophilised);
FCS-buffer (10% FCS, 9 g/l NaCl, Tween 20 0.05%);
concentrated wash solution (20× concentrated);
positive control serum;
negative control serum;
an antibody reacting with the antibody of Multiple Sclerosis [conjugate-(AP conjugated with anti-Igm)];
a substrate (p-nitrophenylphosphate, disodium salt);
a substrate buffer (1 M diethanolamine buffer, pH 9.8);
a stop solution (1 M sodium hydrate).

If preferred the buffer solution for adhering the peptide to the plate and the modified peptide according to the invention can be incorporated directly in the microplate.

Diagnostic Use

For diagnostic use the glycopeptides of the invention were diluted and absorbed onto binding plastic in the wells of microtitre plates (ELISA systems). Patient serum or plasma was then added in a series of different concentrations (dilution series). The autoantibody specific for our products bound to the peptide absorbed onto the plastic. According to the technique known by experts in the field, ELISA (Enzyme Linked Immuno-Sorbent Assay), the autoantibody molecules bound to the glycopeptide are then evidenced through the binding of appropriate secondary antibodies, added to the ELISA plates, which recognise the immunoglobulin constant fragment. These secondary antibodies, conjugated with appropriate enzymes, can be visualised through a colourimetric reaction: the absorbance developed is proportional to the amount of specifically bound autoantibody. Quantitatively, the result is expressed as the antibody titre, defined as the reciprocal of the dilution factor in which no further reaction is observed.

The antibody titre, as defined above, was measured in different patients affected by multiple sclerosis; the glycoproteins according to the invention have shown higher antibody titres compared to those measured with known glycopeptides.

Therapeutic use

The peptides according to the invention, in free form or bound to appropriate resins, can be used for the treatment of patients affected by multiple sclerosis as, thanks to their high specificity of antibody recognition, they can be used to neutralise and/or selectively remove the autoantibodies.

The invention claimed is:

1. Glycopeptides constituted of 11 to 24 amino acids containing a formula (I) tetrapeptide X-Asn(G)-Y-Z    (I)

in which:
X=amino acid carrying an amino or carboxylic group on the side chain;
Y=Pro, Gly;
G=sugar; and
Z=Ala, Val, Ile, His.

2. The glycopeptides according to claim 1 of formula (II):

A-B-X-Asn(G)-Y-Z-C-D    (II)

in which:
Y and G are as defined above;
A is a group of 2 to 5 amino acids or is absent
B and C are trifunctional amino acids capable of forming a lactam bridge between each other by means of the respective side chains or are both absent;
D represents a group of 5 to 15 amino acids;
X is an amino acid selected from the group consisting of Glu, Asp, Lys, Arg, Orn, and Dap; and
Z is an amino acid selected from the group consisting of Ala, Val, Ile, and His.

3. The glycopeptides according to claim 2, in which B and C represent the pairs:
Dap-Asp or Asp-Dap, Dab-Glu or Glu-Dab, Orn-Asp or Asp-Orn and the pairs formed by other amino acids, having analogous characteristics.

4. The glycopeptides according to claim 1, in which the sugar is selected from the group consisting of mono-and disaccharides such as -D-glucopyranosyl (Glc), 2-acetylglucosamina(GlcNAc), cellobiose and analogues.

5. The glycopeptides according to claim 4, wherein the sugar is -D-glucopyranosyl(Glc).

6. The glycopeptides according to claim 1, represented by the following formulae:

H-Thr-Pro-Arg-Val-Glu-Arg-Asn (Glc)-Gly-His-Ser-Val-Phe-Leu-Ala-Pro-Tyr-Gly Trp-Met-Val-Lys-OH (SEQ ID NO: 1)

H-Thr-Pro-Arg-Val-cyclic [Dap-Arg-Asn(Glc)-Gly-His-Asp]-Val-Phe-Leu-Ala-Pro-Tyr-Gly-Trp-Met-Val-Lys-OH (SEQ ID NO: 2)

H-Thr-Pro-Arg-Val-cyclic [Asp-Arg-Asn (Glc)-Gly-His-Orn]-Val-Phe-Leu-Ala-Pro-Tyr Gly-Trp-Met-Val-Lys-OH (SEQ ID NO: 3)

H-Ala-Lys-Thr-Ala-Lys-Asn (Glc)-Gly-His-Val-Glu-Ala-Ser-Gly-OH (SEQ ID NO: 4)

H-Glu-Asn (Glc)-Pro-Val-Val-His-Phe-Phe-Lys-Asn-Ile-Val-Thr-Pro-Arg-Thr-Pro-OH (SEQ ID NO 5)

H-Asp-Asn(Glc)-Pro-Val-Glu-Ala-Phe-Lys-Gly-Ile-Ser-OH (SEQ ID NO: 6)

H-Thr-Pro-Arg-Val-Glu-Arg-Asn (Glc)-Gly-His-Ser-HN-(CH$_2$)$_6$-CO-Val-Phe-Leu-Ala-Pro-Tyr-Gly-Trp-Met-Val-Lys-OH (SEQ ID NO: 7)

H-Asp-Asn(Glc)-Pro-Val-Val-His-Phe-Phe-Lys-Asn-Ile-Val-(Ala)$_3$-OH. (SEQ ID NO: 8).

7. The glycopeptides according to claim 1, containing an alkyl spacer in nonterminal positions.

8. The glycopeptides according to claim 7, in which said alkyl spacer is a group of formula —HN—(CH2)$_n$—CO$_2$— wherein n is comprised between 2 and 6.

9. The glycopeptides according to claim 1, containing a further C-terminal HN—(CH$_2$)$_n$—CO$_2$H group wherein n is comprised between 2 and 6.

10. Process for the solid-phase preparation of glycopeptides according to claim 1, in which:
    a) the C-terminal residue is covalently bound to an appropriate solid support;
    b) the successive amino acids are added sequentially, through acylation of the amino group of the residue bound to the resin;
    c) the crude peptide is recovered by treatment of the resin with an appropriate acid;
    d) the peptide is purified resorting to chromatographic techniques;
    e) the peptide is eventually attached to an appropriate solid support.

11. The process according to claim 10, in which the solid support of stage (a) is selected from the group consisting of silica gel, cellulose, polyacrylate, sepharose and analogues, polystyrene (Wang's® resin), polystyrene-polyoxyethylene (TentaGel® resin or PEG-PS), copolymers of polyethyleneglycol and polyacrylamide (PEGA resin), POEPS (polyoxyethylene-polystyrene), POEPOP (polyoxyethylene polyoxypropylene), SPOCC (PEG substituted with oxethane) and derivatives thereof.

12. The process according to claim 11, in which the solid support of stage (e), if present, is selected from the group consisting of silica gel, cellulose, polyacrylate, and sepharose.

13. Conjugates constituted by a resin, insoluble in water and completely compatible with organic fluids, and a glycopeptide according to claim 1.

14. The conjugates according to claim 13, wherein the resin is selected from the group consisting of sepharose, cellulose and silica gel.

15. Plates for diagnosis containing the glycopeptides according to claim 1.

16. Diagnostic methods for identifying multiple sclerosis antibodies wherein the free glycopeptides according to claim 1 are used.

17. Diagnostic methods for identifying multiple sclerosis antibodies wherein the conjugates according to claim 13 are used.

18. A kit for the diagnosis of Multiple Sclerosis comprising:
- a microplate;
- a buffer solution for adhering the peptide to the plate;
- a modified peptide according to claim 1 (lyophilised);
- FCS-buffer (10% FCS, 9g/l NaCl, Tween 20 0.05%);
- concentrated wash solution (20×concentrated);
- positive control serum;
- negative control serum;
- a human-Igm antibody reacting with the antibodies of Multiple Sclerosis;
- a substrate (p-nitrophenylphosphate, disodium salt);
- a substrate buffer(1 M diethanolamine buffer, pH9.8);
- a stop solution (1 M sodium hydrate).

* * * * *